United States Patent [19]

Schwarz et al.

[11] 4,444,936
[45] Apr. 24, 1984

[54] BIS-(SILYLETHYL)-OLIGOSULPHIDES AND PROCESS FOR THEIR PRODUCTION

[75] Inventors: Rudolf Schwarz, Alzenau-Wasserlos; Peter Kleinschmit, Hanau; Christa Liedtke, Bruchköbel; Siegfried Wolff, Bornheim-Merten, all of Fed. Rep. of Germany

[73] Assignee: Degussa Aktiengesellschaft, Hanau, Fed. Rep. of Germany

[21] Appl. No.: 461,432

[22] Filed: Jan. 27, 1983

Related U.S. Application Data

[62] Division of Ser. No. 282,949, Jul. 13, 1981, Pat. No. 4,384,132, which is a division of Ser. No. 106,862, Dec. 26, 1979, Pat. No. 4,408,064.

[30] Foreign Application Priority Data

Dec. 27, 1978 [DE] Fed. Rep. of Germany ....... 2856229

[51] Int. Cl.$^3$ ............................................. C08K 5/06
[52] U.S. Cl. .................................. 524/393; 524/572; 525/262
[58] Field of Search ....................... 524/572, 373, 393; 525/262

[56] References Cited

U.S. PATENT DOCUMENTS

| | | | |
|---|---|---|---|
| 3,873,489 | 3/1975 | Thurn et al. | 524/393 |
| 3,997,581 | 12/1976 | Pletka et al. | 556/427 |
| 4,072,701 | 2/1978 | Pletka et al. | 556/427 |

Primary Examiner—Joseph L. Schofer
Assistant Examiner—N. Sarofim
Attorney, Agent, or Firm—Cushman, Darby & Cushman

[57] ABSTRACT

Novel bis-(silylethyl)-oligosulphides are obtained by reacting a vinyl silane of the formula $(CH_2=CH)_m-SiR_n^1R_{4-(m+n)}$ in which R represents chlorine, bromine, iodine, $C_1$—$C_3$-alkoxy, 2-methoxyethoxy, 2-ethoxyethoxy or hydroxy, $R^1$ represents $C_1$—$C_3$-alkyl, phenyl or $C_5$—$C_7$-cycloalkyl, n is 0, 1 or 2, m is 1 or 2 and m+n is 1, 2 or 3 with sulphur as well as in a given case hydrogen sulphide in molar ratios of vinyl silane to sulphur of from 1:2.5 to 1:10 and vinyl silane to hydrogen sulphide of from 1:0 to 1:5 at temperatures between about 100° and 200° C. under pressure of from 1 to 25 bars (total pressure at the reaction) temperature) and in the presence of sulphidation catalysts known per se, in a given case followed by hydrolysis or partial hydrolysis of the reaction products. The bis-(silylethyl)-oligosulphides are used as reinforcing additives (adhesive agents) in crosslinkable rubber mixtures containing silicate fillers and in a given case carbon black as well as in a given case sulphur and other customary constituents.

21 Claims, 5 Drawing Figures

BIS-(SILYLETHYL)-OLIGOSULPHIDES AND PROCESS FOR THEIR PRODUCTION

This is a division of application Ser. No. 282,949 U.S. Pat. No. 4,384,132, filed July 13, 1981 which is a div. of Ser. No. 106,862 filed Dec. 26, 1979 U.S. Pat. No. 4,408,064.

BACKGROUND OF THE INVENTION

It is known that bis-(alkoxysilylalkyl)-oligosulphides can be produced from the corresponding alkoxy silyl alkyl mercaptans by direct reaction with sulphur (German Pat. No. 2,405,758 and related Pletka U.S. Pat. No. 3,997,581. The entire disclosure of Pletka is hereby incorporated by reference and relied upon.) The same oligosulphidic silanes can be obtained even more simply and conveniently from the alkoxy silyl alkyl halides by a single reaction with, in particular, alkali metal hydrogen sulphides and sulphur. In this case, excess hydrogen sulphide is formed (German Offenlegungsschrift No. 2,542,534 and related Pletka U.S. Pat. No. 4,072,701. The entire disclosure of this Pletka patent is hereby incorporated by reference and relied upon.)

It is also known that bis-(alkoxysilylalkyl)-oligosulphides can be produced from the corresponding disulphides by reaction with sulphur at temperatures in the range from 100° to 200° C. (German Offenlegungsschrift No. 2,360,471).

All the above-mentioned oligosulphides contain up to at most 6 sulphur atoms forming as it were a bridge between the two alkyl groups attached to the silicon, the alkyl groups containing from 1 to 10 carbon atoms.

Finally, it is known that silyl alkyl thioethers can be obtained from vinyl silanes by reaction with hydrogen sulphide (German Auslegeschrift No. 1,000,817).

Oligosulphidic silanes have acquired considerable significance as additives in rubber mixtures containing silica filler inter alia for improving the mechanical properties of the vulcanisates (German Pat. No. 2,255,577 and related Thurn U.S. Pat. No. 3,873,489. The entire disclosure of Thurn is hereby incorporated by reference and relied upon.)

It is also possible to introduce sulphur-free silanes containing unsaturated organic groups as ligand on the silicon atom into mixtures based on certain rubbers. It is also known that silyl alkyl thioethers do not produce any advantageous rubber properties in vulcanisates and that, among other disadvantages, mercapto silanes give off an intense, very unpleasant odor.

An object of the present invention is to provide a new and useful process for the production of sulphur-containing silanes which may be easily and effectively incorporated for example into rubber mixtures containing silicate fillers and which inter alia impart particularly favorable properties to the vulcanisates obtained therefrom.

Another object is to develop novel sulphur containing silanes.

A further object is to prepare novel rubber mixtures containing such sulphur containing silanes and silicate fillers with or without sulphur and with or without carbon black.

SUMMARY OF THE INVENTION

It has now been found that novel bis-(silylethyl)-oligosulphides containing up to more than 6 sulphur atoms, e.g. 6.9 or more sulphur atoms, or even more than 7 sulphur atoms and even up to 8 sulphur atoms can be produced by the new process.

According to the invention there are obtained bis-(silylethyl)-oligosulphides corresponding to the following average formula:

$$\{R_{4-(m+n)}R^1_n Si[CH_2CH_2]_m\}_2 S_{mx} \qquad I$$

in which
R represents chlorine, bromine, iodine, $C_1$- to $C_3$-alkoxy, 2-methoxyethoxy, 2-ethoxyethoxy or hydroxy,
$R^1$ represents $C_1$- to $C_3$-alkyl, phenyl or $C_5$- to $C_7$-cycloalkyl,
n=0, 1 or 2,
m=1 or 2, m+n=1, 2 or 3, and
x=2.0 to 8.0,
by reacting a vinyl silane corresponding to the following formula $$(CH_2=CH)_m-SiR^1_n R_{4-(m+n)} \qquad II$$

in which R, $R^1$, n and m are as defined above, with sulphur and, optionally, hydrogen sulphide in molar ratios of vinyl silane to sulphur of from 1:2.5 to 1:10 and vinyl silane to hydrogen sulphide of from 1:0 to 1:5 at a temperature in the range from about 100° to 210° C., under a pressure of from 1 to 25 bars (total pressure at the reaction temperature) and in the presence of a sulphidation (+) catalyst known per se, optionally followed by hydrolysis or partial hydrolysis of the reaction products.
(+) also called sulfurization The bis-(silylethyl)-oligosulphides are useful as reinforcing additives (adhesion promoters) in cross-linkable rubber mixtures containing siliceous fillers, optionally carbon black and, optionally, sulphur and other standard constituents.

It has been found that the products obtained by the process according to the invention are not identical with the known, above-mentioned oligosulphidic silanes (German Offenlegungsschrift No. 2,542,534 and Pletka U.S. Pat. No. 4,072,701). Compared with the additives according to the above-mentioned German Pat. No. 2,255,577 and Thurn U.S. Pat. No. 3,873,489, the silanes produced by the process according to the invention enable substantially the same outstanding and, in some cases, even better results to be obtained in rubber mixtures and their vulcanisates.

In general terms, the new process effects the addition of sulphur with organosilanes containing ethylenically unsaturated organic groups and is preferably carried out under autogenous pressure(+) and elevated temperature. During the reaction, which alternatively may even be carried out in the presence of hydrogen sulphide, the elemental sulphur is apparently incorporated into the organosilane molecule in such a way that sulphur bridges containing more than one sulphur atom in the molecule, depending on the quantity of sulphur used, are formed.
(+) i.e. the self-arising pressure in the closed vessel while the reaction is going on It is assumed that, where in particular relatively large quantities of sulphur are used, some of the sulphur is incorporated in the form of chain branching of the sulphur bridge between the silyl alkyl groups. Even if hydrogen sulphide is not additionally used, sulphur-containing compounds and compound mixtures are evidently formed and, by comparison with known oligosulphidic silanes, produce equally good and, in some cases, even better processing properties of rubber moulding compositions and also rubber properties of vulcanisates produced therefrom, the reactions both with and also without hydrogen sulphide being carried out under pressure and a temperature which is generally above the boiling temperature of the corresponding silane starting compounds.

It is possible by the process according to the invention to produce silanes containing up to 8 sulphur atoms in the molecule, even if only one unsaturated organic group is available per silane starting molecule. However, it has been found that the quantity of sulphur used can reach an optimum in terms of practical application. In general, this optimum quantity amounts to approximately 7.5 moles of elemental sulphur per mole of silane used and is governed to some extent by the particular silane reacted. A quantity of sulphur distinctly in excess of this optimum quantity does not afford any significant advantages in terms of rubber technology, but only makes the reaction mixtures difficult to work up because the unreacted sulphur or the sulphur which is separated again after cooling of the reaction products has to be removed, for example by filtration.

Of the total sulphur content of the synthesized compounds, the analytically determinable polysulphidically bound sulphur[+] is particularly effective in terms of practical application, particularly in rubber technology.
[+] i.e. sulphur which is bound to sulphur only NMR-spectra were recorded from the silanes produced in accordance with the invention. Their evaluation suggests the conclusion that, in consequence of the reaction without hydrogen sulphide, the arrangement of the sulphur atoms in the silanes is far less defined and established than where the alternative reaction is adopted, in respect of which it is assumed that the addition of hydrogen sulphide to the double bond of the unsaturated compounds with primary formation of the corresponding mercaptan takes place in a first stage and the following addition of the mercaptan primarily formed to a double bond of another molecule with simultaneous incorporation of elemental sulphur into the chain takes place in a second stage.

It has been found that, even at greatly increased temperature and pressure, the above-mentioned reactions do not take place to any significant extent or at a sufficient velocity or in such a favorable direction in terms of rubber technology if they are carried out in the absence of a catalyst. It has been found that alkaline acting substances, such as alkalis, amines, quaternary ammonium compounds and, above all, alkali metal alkoxides such as sodium ethylate, potassium ethylate, sodium methylate, sodium isopropylate, potassium propylate, sodium butylate etc., are particularly suitable catalysts.

Illustrative of alkalis and amines and quaternary ammonium compounds are sodium hydroxide, potassium hydroxide, n-propyl amine, n-butyl amine, ethyl amine, dodecyl amine, trimethyl amine, triethyl amine, tributyl amine, triamyl amine, trioctyl amine, tetramethyl ammonium hydroxide, tetraethyl ammonium hydroxide, cetyl pyridinium hydroxide. Even where hydroquinones are used as catalysts, equally good results are obtained, particularly where hydroquinone itself is used. Other hydroquinones includes for example 2-methyl hydroquinone, 2-ethyl hydroquinone, 2-butyl hydroquinone and other 2-alkyl hydroquinones.

The temperature may be varied within relatively wide limits of from about 100° to 200° or even 210° C. without adversely affecting the quality of the reaction products and, as usual, is related to the reaction time. A combination of a reaction temperature of 150° C. and a reaction time of 7 hours proved to be particularly advantageous. Below a temperature of about 100° C., the reaction gives a product with no value in terms of rubber technology. At reaction temperatures distinctly above 200° C., for example at around 250° C., the reaction products begin to decompose.

The reaction pressure, i.e. the total pressure prevailing at the particular reaction temperature, can also vary within wide limits, i.e. between about 1 and 25 bars. It may be adjusted for example by the introduction of hydrogen sulphide under pressure. In general, the autogenous pressure is sufficient.

The molar ratio of silane to sulphur is selected according to the required amount of sulphur in the molecule of the silane according to the invention and amounts to between 1:2.5 and 1:10.

Where hydrogen sulphide is additionally used, the molar ratio of vinyl silane to hydrogen sulphide may amount to between about 1:0.1 (1:0 signifies the absence of $H_2S$) and 1:5.

During the reaction, it is particularly important to ensure, by using suitable apparatus, that the elemental sulphur which is liquid at the elevated reaction temperature is more effectively reacted with the silane by intensive mixing. On completion of the reaction, the reaction mixture is left to cool with continued stirring and further processing in the same way as described in the Examples.

The following are examples of vinyl silanes corresponding to formula II: vinyl trichlorosilane, vinyl methyl dichlorosilane, vinyl phenyl dichlorosilane, vinyl diphenyl chlorosilane, vinyl dimethyl chlorosilane, vinyl trimethoxy silane, vinyl triethoxy silane, vinyl tripropoxysilane, vinyl-tris-i-propoxy silane, vinyl-tris-(2-methoxyethoxy)-silane, divinyl dichlorosilane, divinyl dibromosilane and diiodosilane, vinyl dimethyl hydroxy silane, vinyl propyl diethoxy silane, vinyl dicyclohexyl chlorosilane, divinyl diethoxy silane, divinyl dimethoxy silane, divinyl-di-i-propoxy silane, divinyl-di-n-propoxy silane, vinyl methyl dimethoxy silane, vinyl ethyl diethoxy silane, vinyl methyl-di-(2-ethoxy)-silane, vinyl diethyl ethoxy silane, vinyl dimethyl methoxy silane, vinyl diethyl-2-methoxy ethoxy silane, vinyl phenyl diethoxy silane, vinyl diphenyl methoxy silane, vinyl cyclohexyl diethoxy silane, vinyl cyclopentyl diethoxy silane and vinyl cycloheptyl dimethoxy silane. It is preferred to use monovinyl silanes.

The optional hydrolysis or partial hydrolysis of the reaction products obtained in accordance with the invention is carried out by methods known per se, hydrolysable groups R being converted into hydroxy groups.

The term "siliceous filler" is a broad term and refers to fillers which are rubber compatible or can be worked into rubber mixtures which fillers consist of silicates or silica, or contain silicates or silica and/or contain chemically bound silicates (or silica) in the widest sense, including mixtures of two or more siliceous fillers. Especially counted as siliceous fillers are:

Highly dispersed silica (silicon dioxide) having a specific surface area in the range of about 5 to 1000, preferably 20 to 400 m$^2$/g (determined with gaseous nitrogen according to the known BET procedure) and with primary particle sizes in the range of about 10 to 400 nm. (nanometer, $10^{-9}$ meters), which can be produced, for example, by precipitation from solutions of silicates, by hydrolysis and/or oxidative high temperature conversion. There can also be used flame hydrolysis of volatile silicon halides, e.g., silicon tetrachloride, or by electric arc processes. These silicas, in a given case, can also be present as mixed oxides or oxide mixtures with oxides of the metals aluminum (alumina), magnesium (magnesium oxide), calcium (calcium oxide), barium (barium oxide), zinc (zinc oxide), zirconium (e.g., zirconium dioxide), or titanium (e.g., titanium dioxide).

Synthetic silicates, for example, aluminum silicate or alkaline earth silicates such as magnesium, or calcium silicate with specific surface areas of about 20 to 400 m$^2$/g and primary particle sizes of about 10 to 400 nm.

Natural silicates, for example, kaolin, wollastonite, talc and asbestos as well as natural silicas, e.g., quartz or sand.

Glass fibers and glass fiber products such as mats, webs, strands, fabrics, non-woven fabrics and the like as well as microglass balls (microglass balloons).

The siliceous fillers mentioned can be added in amounts of about 10 or, in a given case, even less, up to about 250 parts by weight based on 100 parts by weight of rubber polymer.

As filler mixtures there can be used, for example, silica-kaolin or silica-glass fibers-asbestos, as well as blends of siliceous reinforcing fillers with the mentioned rubber blacks, for example, silica-ISAF carbon black or silica-glass fiber cords HAF carbon black.

Typical examples of siliceous fillers usable in the invention, for example, are those produced by Degussa, such as silica or silicates under the tradenames; Aerosil, Ultrasil, Silteg, Durosil, Extrusil, Calsil, etc.

Furthermore there can be mixed into the rubber mixtures various additives which are well known in the rubber industry and widely used.

The new silanes used in the invention can be added to the rubber mixture in amounts of 0.1 to 50 parts by weight, preferably within the limits of 0.5 to 25 parts by weight based on 100 parts by weight of rubber.

Unless otherwise indicated all parts and percentages are by weight.

The rubber mixture can be produced with one or more, in a given case oil-extended, natural and/or synthetic rubbers. These include especially natural rubber, synthetic rubbers, preferably diene elastomers as for example polybutadiene, polyisoprene, e.g., cis-polyisoprene, butadiene-styrene copolymer, butadiene-acrylonitrile copolymer, polymerized 2-chlorobutadiene, also butyl rubber, halogenated butyl rubber such as chlorinated butyl rubber, brominated butyl rubber as well as other known diene rubbers as for example terpolymers of ethylene, propylene and for example non-conjugated dienes and also non-conjugated polyenes, e.g., ethylene-propylene-cyclooctadiene, ethylenepropylene-norbornadiene, ethylene-propylene dicyclopentadiene and ethylene-propylene-cyclododecatriene. Also there can be used trans-polypentenamer, carboxy or epoxy rubbers and the like known elastomers. The chemical derivatives of natural rubber and modified natural rubber can also be used in the invention.

All the 60 MHz H$^1$-NMR-spectra reproduced in the Figures were recorded under the following conditions: solvent CDCl$_3$; temperature 37° C.; filter band width 4 Hz; R.F. field 0.02 mG; recording time 250 s; recording range 500 Hz; spectrum amplitude 8. The internal standard was tetramethyl silane (δ—value=0). The curve of the NMR-spectrum includes the integration curve which is also reproduced.

DESCRIPTION OF THE PREFERRED EMBODIMENTS

EXAMPLE 1

In a 1.5-liter capacity stirrer-equipped vessel, 300 g of sulphur in powder form (corresponding to 9.37 moles) are dispersed in 238 g of vinyl triethoxy silane (1.25 moles) by means of a blade stirrer. The resulting dispersion is introduced into a 2-liter capacity pressure vessel equipped with an automatic stirrer. Following the addition of 12 g of hydroquinone as catalyst, the pressure vessel is closed and its contents heated to 150° C. over a period of 30 minutes during which the pressure rises to around 5 bars. The reaction is continued under these conditions for 7 hours with intensive stirring. The reaction mixture is then cooled and the contents of the vessel relieved of pressure. The unreacted sulphur is filtered off. The residual reaction product is a pale reddish-brown, clear slightly oily liquid which has a total sulphur content of 39.1% by weight and a polysulphur content of 24.9% by weight. Unsaturated carbon atoms emanating from the vinyl groups can no longer be detected.

Practical testing of the reaction product in a styrene-butadiene rubber test mixture containing silica filler both with conventional crosslinking with sulphur and also with elemental-sulphur-free crosslinking with the sulphur-containing reaction product revealed an increase in tensile strength by comparison with a conventional oligosulphidic silane, coupled with equally good or improved moduli and distinctly increased rate of reaction. x (see formula I)=7.6.

EXAMPLE 2

Figure 1:
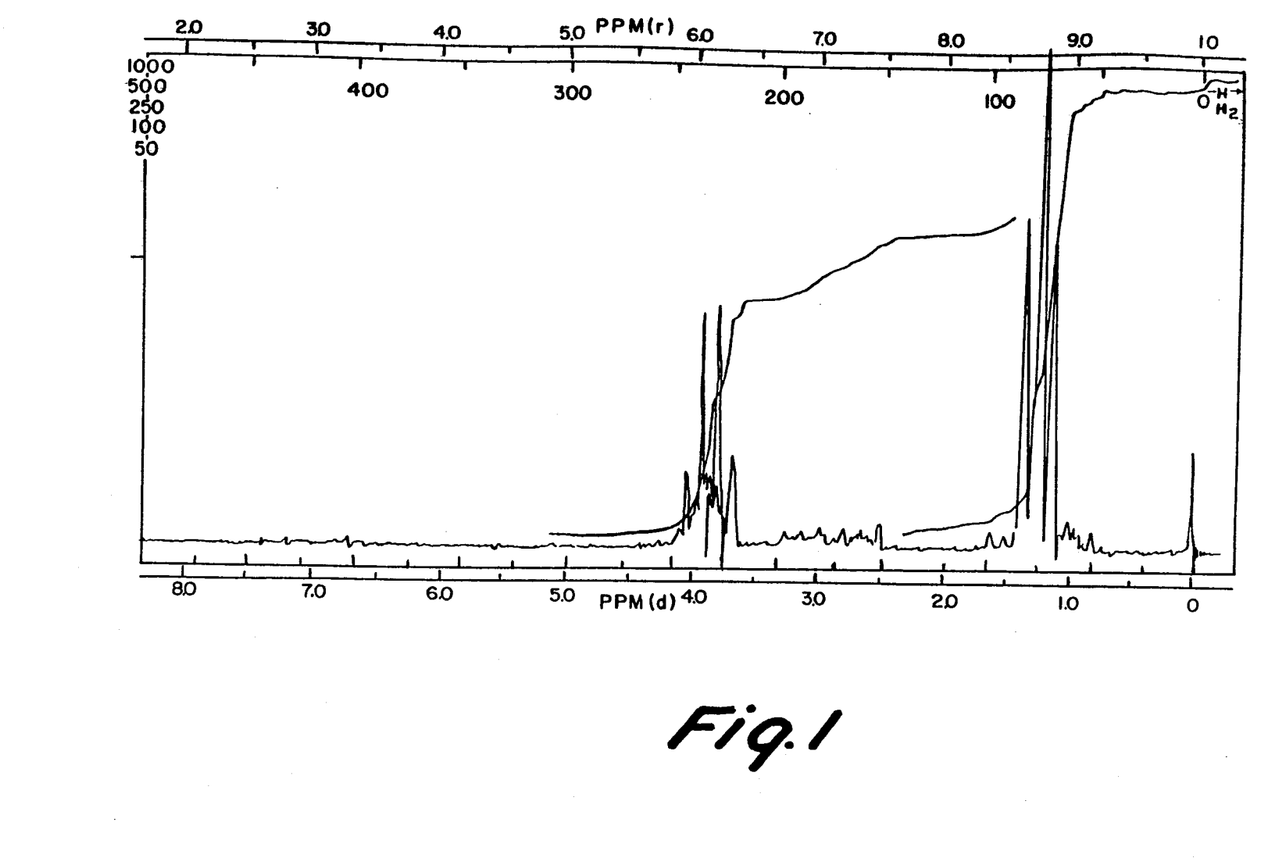
FIG. 1 is the NMR-spectrum of the product prepared in Example 2.

The procedure was as in Example 1, except that, before heating, hydrogen sulphide was introduced into the autoclave up to a pressure of 10 bars. The reaction time and temperature were the same. The total sulphur content of the filtered, clear reaction product now amounted to 27.6% by weight and the content of polysulphidic sulphur to 17.6% by weight. The NMR-spectrum of the reaction product is shown in FIG. 1. x=4.5.

Practical rubber testing in accordance with Example 1 showed that, again by comparison with a conventional oligosulphidic silane, the reaction product produced with the additional use of H$_2$S brings about a distinct increase in the rate of reaction both when vulcanization is carried out with sulphur and when crosslinking is carried out in the absence of elemental sulphur. At the same time, the tensile strength (DIN 53 504) (German Industrial Standard 53504) of the vulcanisate or crosslinked product is increased whereas the measured values for the moduli, resilience (ASTM D 624) and tear propagation resistance (DIN 53 507) reach or almost reach the already very good values of the comparison silane.

EXAMPLE 3

Figure 2:
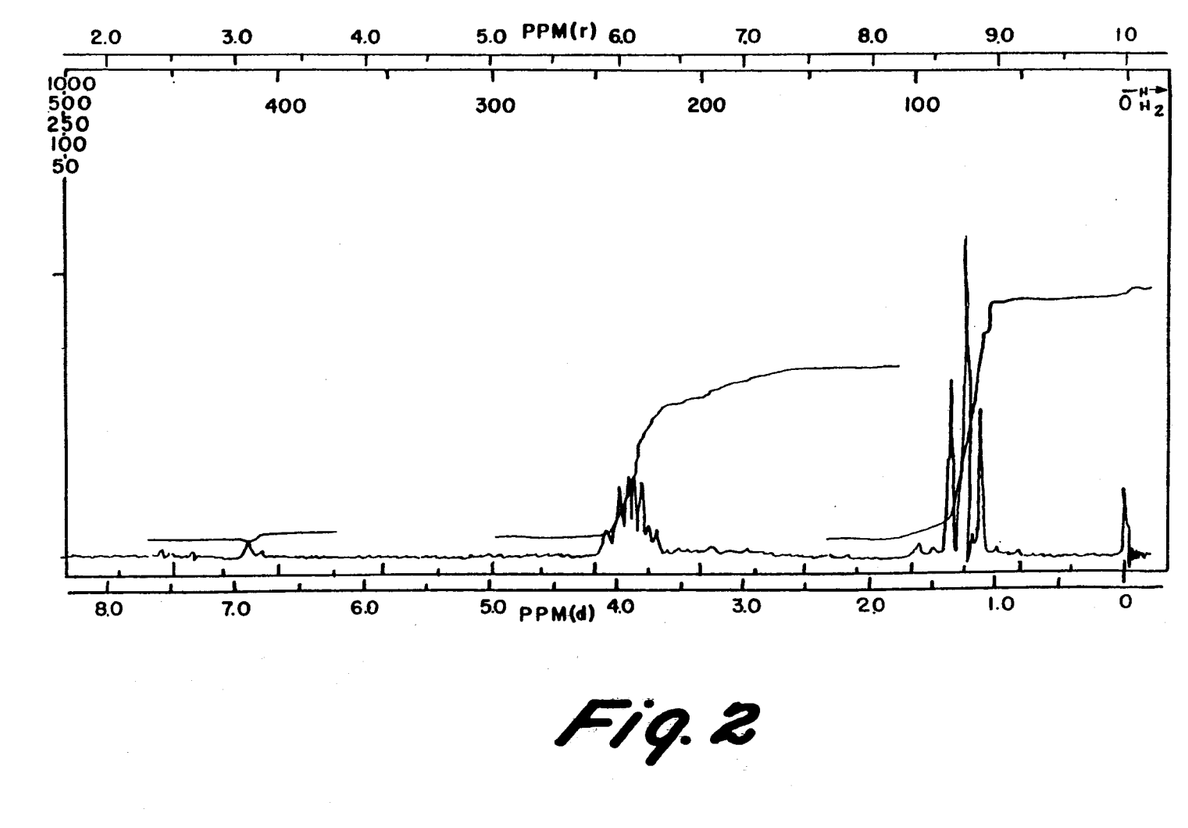
FIG. 2 is the NMR-spectrum of the product prepared in Example 3.

If the procedure of Example 1 is repeated under the same conditions, but with vinyl silane and sulphur in a molar ratio of 1:10, a reaction product is obtained which contains 33.4% by weight of total sulphur and 18.8% by weight of polysulphidic sulphur and of which the NMR-spectrum is shown in FIG. 2. The practical rubber testing of this reaction product again shows improved test values by comparison with said known oligosulphidic silane. The increase in the rate of reaction by the reaction product both with sulphur-containing and with sulphur-free crosslinking of the shaped rubber compositions is again remarkable. x=6.0.

EXAMPLE 4

Figure 3:
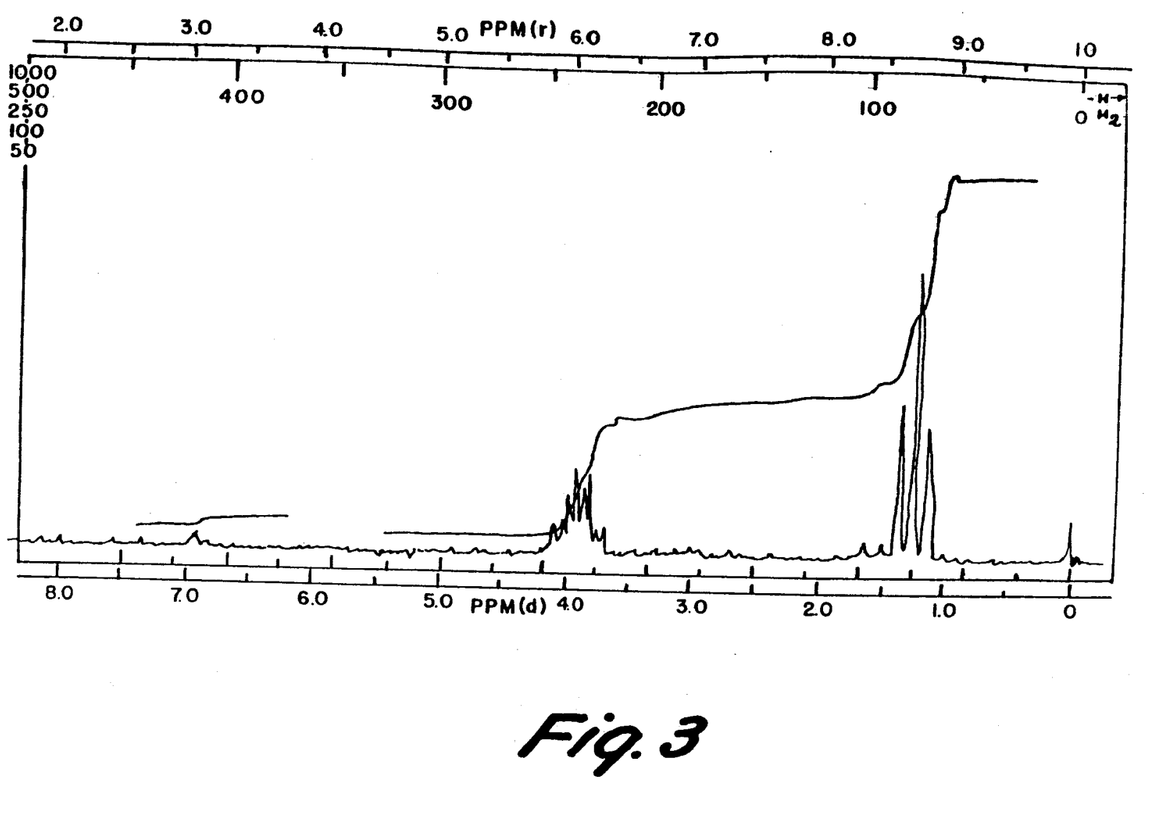
FIG. 3 is the NMR-spectrum of the product prepared in Example 4.

If the procedure of Example 3 is repeated with only the reaction time being increased (to 21 hours), a reaction product is obtained which has an increased content of polysulphidic sulphur (20.1% by weight), but a lower total sulphur content (30.7% by weight). The NMR-spectrum of this product is shown in FIG. 3. x=5.2.

Testing of the reaction product in rubber molding compositions and vulcanisates again shows good results, such as in particular an increase in the rate of reaction and an increase in the tensile strengths after vulcanization (sulphur-free and sulphur-containing) and, for example, an increase in tear propagation resistance (DIN 53 507) after sulphur-free crosslinking.

EXAMPLE 5

Figure 4:
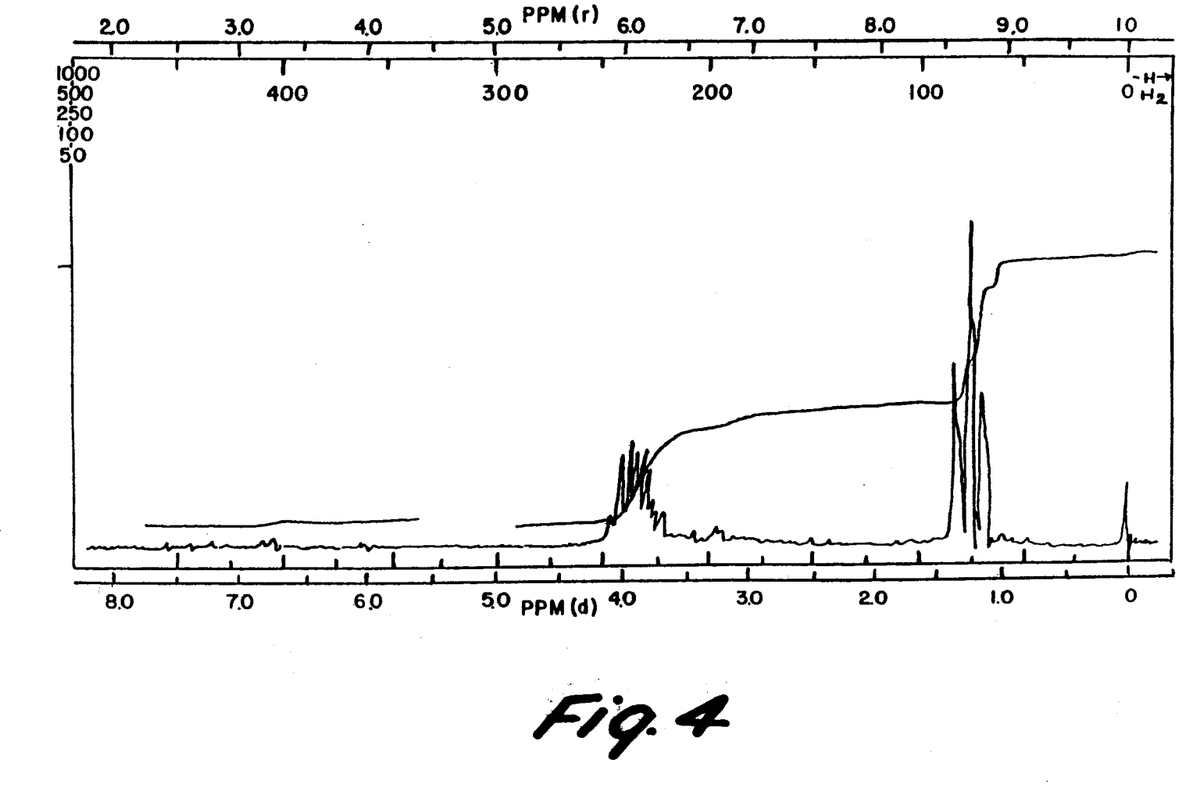
FIG. 4 is the NMR-spectrum of the product prepared in Example 5.

A reaction product is again prepared under the same conditions and using the same quantities as in Examples 1 and 3, but with a ratio of vinyl triethoxy silane to sulphur of 1:5. It has a total sulphur content of 36.6% by weight and a polysulphidic sulphur content of 22.9% by weight. The NMR-spectrum of this reaction product is shown in FIG. 4. The high sulphur content of both types gives particularly advantageous results in practical rubber testing: an increased rate of reaction by comparison with the results obtained with the known oligosulphidic silane Si 69; also a more favorable crosslinking yield, particularly where vulcanization is carried out with sulphur, a improved tensile strength (DIN 53 504), at least equally good moduli and tear propagation resistances (DIN 53 507) and slight increases in Shore A hardness. Silane Si 69 is bis-(3-triethoxysilylpropyl)-oligosulphide having a sulphur content of at least 22.0 weight percent made f.i. by Pletka U.S. Pat. No. 4,072,701, e.g. Example 1 thereof.

EXAMPLE 6

Figure 5:
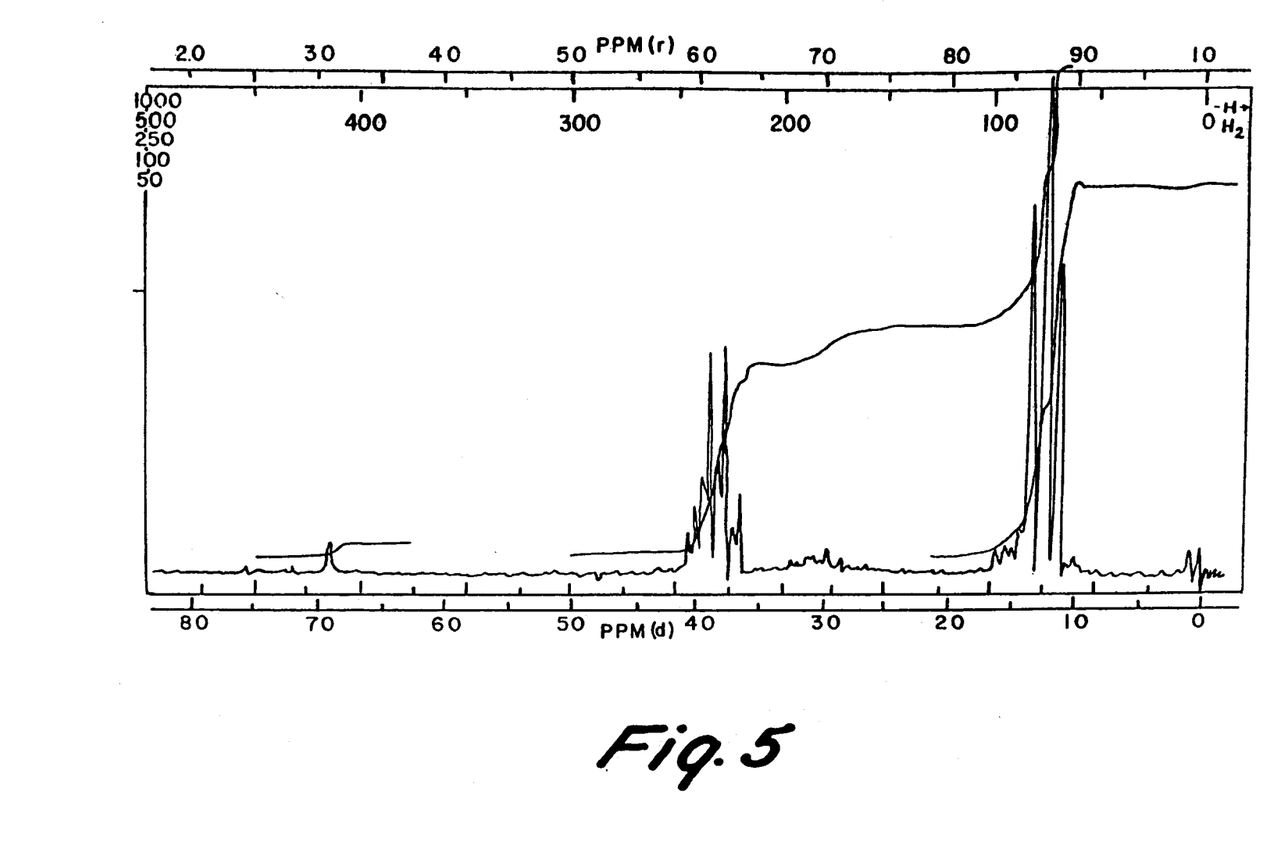
FIG. 5 is the NMR-spectrum of the product prepared in Example 6.

Following the procedure of Example 2, a reaction product was produced with the following modifications, hydrogen sulphide being additionally used: $H_2S$-pressure 11 bars, reaction temperature 200° C. (reaction time: 7 hours), vinyl triethoxy silane and sulphur in a molar ratio of 1:10. The reaction product had a total sulphur content of 25.2 and a polysulphidic sulphur content of 14.5% by weight. Its NMR-spectrum is shown in FIG. 5.

The practical rubber testing of this reaction product shows that the measured values are at the same level as the corresponding values of Example 2, being more favorable in some instances (rate of reaction, tear propagation resistance) and less favorable in others (tensile strength, moduli).

The composition of the invention can comprise, consist essentially of or consist of the materials set forth and the process can comprise, consist essentially of or consist of the steps set forth with such materials.

The above examples are summarized in following Table 1.

TABLE 1

| Example | 1 | 2 | 3 | 4 | 5 | 6 |
|---|---|---|---|---|---|---|
| Total Sulphur Content | 39.1 | 27.6 | 33.4 | 30.7 | 36.6 | 25.2 |
| x (Calculated from sulphur content) | 7.6 | 4.5 | 6.0 | 5.2 | 6.9 | 4.0 |

The use of the silanes of the invention and the demonstration of the superior effect of the same is shown by the test results in Table 3 of the vulcanizates or crosslinked products of the compositions of Table 2.

In Table 2 the silica filler was an active silica produced by precipitation and having a specific surface (DIN 66132) of 175 $m^2/g$ and an average primary particle size of 18 microns. Silane Si 69 has been identified above.

TABLE 2

| Constituents | V 1 | E 1.1 | E 2.1 | E 3.1 | E 4.1 | E 5.1 | E 6.1 | V 2 | E 1.2 | E 2.2 | E 3.2 | E 4.2 | E 5.2 | E 6.2 |
|---|---|---|---|---|---|---|---|---|---|---|---|---|---|---|
| Styrene-Butadiene Rubber (SBR 1500) | 100 | 100 | 100 | 100 | 100 | 100 | 100 | 100 | 100 | 100 | 100 | 100 | 100 | 100 |
| Silica filler | 40 | 40 | 40 | 40 | 40 | 40 | 40 | 40 | 40 | 40 | 40 | 40 | 40 | 40 |
| Zinc oxide Seal Quality | 3 | 3 | 3 | 3 | 3 | 3 | 3 | 3 | 3 | 3 | 3 | 3 | 3 | 3 |
| Stearic acid | 2 | 2 | 2 | 2 | 2 | 2 | 2 | 2 | 2 | 2 | 2 | 2 | 2 | 2 |
| Silane Si 69 | 3 | — | — | — | — | — | — | 3 | — | — | — | — | — | — |
| Silane according to Example 1 | — | 3 | — | — | — | — | — | — | 3 | — | — | — | — | — |
| Silane according to Example 2 | — | — | 3 | — | — | — | — | — | — | 3 | — | — | — | — |
| Silane according to Example 3 | — | — | — | 3 | — | — | — | — | — | — | 3 | — | — | — |
| Silane according to Example 4 | — | — | — | — | 3 | — | — | — | — | — | — | 3 | — | — |
| Silane according to Example 5 | — | — | — | — | — | 3 | — | — | — | — | — | — | 3 | — |
| Silane according to Example 6 | — | — | — | — | — | — | 3 | — | — | — | — | — | — | 3 |
| N,N'—Dimethyl-N,N'—Diphenyl-thiuramdisul- | — | — | — | — | — | — | 2 | 2 | 2 | 2 | 2 | 2 | 2 | 2 |

TABLE 2-continued

| Constituents | Mixture No. (Amounts in Parts by Weight) | | | | | | | | | | | | | |
|---|---|---|---|---|---|---|---|---|---|---|---|---|---|---|
| | V 1. | E 1.1 | E 2.1 | E 3.1 | E 4.1 | E 5.1 | E 6.1 | V 2 | E 1.2 | E 2.2 | E 3.2 | E 4.2 | E 5.2 | E 6.2 |
| phide | | | | | | | | | | | | | | |
| Benzothiazyl-2cycloheyl-sulphenamide | 1 | 1 | 1 | 1 | 1 | 1 | 1 | — | — | — | — | — | — | — |
| Sulphur | 2 | 2 | 2 | 2 | 2 | 2 | 2 | — | — | — | — | — | — | — |

TABLE 3

RESULTS OF MEASUREMENTS MIXTURE OR ITS VULCANISATE

| Tests and Determinations | V 1. | E 1.1 | E 2.1 | E 3.1 | E 4.1 | E 5.1 | E 6.1 | V 2. | E 1.2 | E 2.2 | E 3.2 | E 4.2 | E 5.2 | E 6.2 |
|---|---|---|---|---|---|---|---|---|---|---|---|---|---|---|
| t 90%-t 10% | 28.8 | 18.1 | 22.4 | 21.2 | 22.3 | 22.6 | 21.6 | 8.8 | 3.6 | 5.5 | 4.0 | 4.5 | 3.8 | 4.8 |
| Tensile Strength | 14.4 | 18.2 | 18.5 | 15.5 | 18.6 | 18.3 | 17.4 | 18.7 | 20.3 | 23.0 | 18.8 | 19.6 | 17.4 | 22.8 |
| Modulus 300% | 5.9 | 6.3 | 5.4 | 5.8 | 5.7 | 5.9 | 5.7 | 5.9 | 5.7 | 5.5 | 5.8 | 5.3 | 6.3 | 4.7 |
| Tear Propagation Resistance | 16 | 14 | 19 | 16 | 17 | 16 | 20 | 16 | 17 | 19 | 22 | 23 | 18 | 24 |
| Shore A Hardness | 64 | 67 | 64 | 67 | 64 | 66 | 64 | 65 | 67 | 66 | 65 | 65 | 67 | 64 |

In Tables 2 and 3 the first half of the rubber mixtures with the comparison mixture V I according to the state of the art and the mixtures of the invention (using the new silane in rubber mixtures) E 1.1 to E 6.1 with the new silanes of production Examples 1 to 6 are vulcanized conventionally with sulphur and accelerators. The second half of the rubber mixtures with the comparison mixture V 2 according to a more recent state of the art procedure (see e.g. German Pat. No. 2,536,674, British Pat. No. 1,524,077 and related Wolff U.S. application Ser. No. 34,203 filed Apr. 27, 1979) and the mixtures E 1.2 to E 6.2 of the invention likewise with the new silanes according to production examples 1 to 6 are cross-linked without elemental sulphur with the aid of the oligosulphidic silanes in the presence of an accelerator.

The tests of the rubber mixtures (as e.g. of the cross-linking kinetics) were carried out according to DIN 53 529 (Preliminary Standard of October 1972) with the title "Vulkametrie" (also called Rheometer test) (Amplitude of Deformation: 3°. Test frequency: 3 cycles per minute. Test temperature: 155° C. Rheometer of Monsanto Co., Type MPV). In the tables t 10% signifies the reaction time (vulcanization time) up to 10% yield in minutes and t 90% the reaction time up to the corresponding 90% yield. The difference t 90%−t 10% is a measure for the rate of reaction and shorter times show a higher rate of reaction.

The measurements of the tensile strengths and moduli (both measured in MPa) of the corresponding vulcanizates or cross-linked products (vulcanization or cross-linking temperature 155° C.) were carried out according to DIN 53 504, the tear propagation resistance carried out according to DIN 53 507 and the Shore A hardness according to DIN 53 505.

The evaluation of the test results is given above in the specification in connection with the production examples, e.g. in Example 1 second paragraph.

The entire disclosure of German priority application P 28 56 229.0-42 is hereby incorporated by reference.

What is claimed is:

1. In a rubber composition comprising a cross-linkable rubber, a siliceous filler and a bis-(silylethyl)-oligosulphide, the improvement comprising having present as the oligosulphide a bis-(silyethyl)-oligosulphide corresponding to the following average formula:

$$R_{4-(m+n)}R_n{}^1Si[CH_2CH_2]_m\ 2^S{}_{mx} \quad I$$

in which R represents chlorine, bromine, iodine, $C_1$–$C_3$-alkoxy, 2-methoxy ethoxy, 2-ethoxy ethoxy or hydroxy, $R^1$ represents $C_1$–$C_3$-alkyl, phenyl or $C_5$–$C_7$-cycloalkyl, n=0, 1 or 2, m=1 or 2, m+n=1, 2 or 3, and x=2.0 to 8.0 by reacting a vinyl silane corresponding to the following formula:

$$(CH_2{=}CH)_m{-}SiR_n{}^1R_{4-(m+n)} \quad II$$

in which R, $R^1$, n and m are as defined above, with sulphur and, optionally, hydrogen sulphide in molar ratios of vinyl silane to sulphur of from 1:2.5 to 1:10 and vinyl silane to hydrogen sulphide of from 1:0 to 1:5 at a temperature in the range from about 100° to 210° C., under a pressure of from 1 to 25 bars (total pressure at the reaction temperature) and in the presence of a sulphidation catalyst or a bis-(silylethyl)-oligosulphide prepared by at least partially hydrolyzing the R group of the oligosulphide of formula I.

2. A rubber composition according to claim 1 wherein x is between 6.9 and 8.0.

3. A rubber composition according to claim 2 wherein x is between 7.0 and 8.0.

4. A rubber composition according to claim 3 wherein x is about 7.5.

5. A rubber composition according to claim 1 wherein the oligosulphide is prepared in the absence of hydrogen sulphide.

6. A rubber composition according to claim 1 wherein the oligosulphide is prepared in the presence of hydrogen sulphide there being employed 0.1 to 5 moles of hydrogen sulphide per mole of vinyl silane.

7. A rubber composition according to claim 1 wherein there is no hydrolysis in making the oligosulphide.

8. A compound according to claim 1 wherein R is $C_1$–$C_3$-alkoxy or chlorine, n is 0 and m is 1.

9. A compound according to claim 8 wherein R is $C_1$–$C_3$ alkoxy.

10. A compound according to claim 9 wherein R is ethoxy.

11. A compound according to claim 10 wherein x is between 6.9 and 8.0.

12. A compound according to claim 11 wherein x is about 7.6.

13. A rubber composition according to claim 1 wherein the rubber is natural rubber, polybutadiene, polyisoprene, butadiene-styrene copolymer, butadiene-acrylonitrile copolymer or ethylene-propylene non-conjugated polyene terpolymer.

14. A rubber composition according to claim 1 wherein the rubber is a sulphur curable rubber and the composition includes sulphur.

15. A rubber composition according to claim 1 wherein the rubber is a sulphur curable rubber and the composition is free from sulphur and the sole crosslinking agent present is said bis-(silylethyl)-oligosulphide.

16. A rubber composition according to claim 14 wherein the siliceous filler is silica or a silicate.

17. A crosslinked rubber produced by curing the composition of claim 1.

18. A rubber composition according to claim 1 wherein x is 6.9 to 8.0.

19. A rubber composition according to claim 1 wherein R is $C_1$–$C_3$-alkoxy or chlorine, n is 0 and m is 1.

20. A rubber composition according to claim 19 wherein R is $C_1$–$C_3$-alkoxy or chlorine, n is 0 and m is 1.

* * * * *